US008452385B2

(12) United States Patent
Lee et al.

(10) Patent No.: US 8,452,385 B2
(45) Date of Patent: May 28, 2013

(54) METHOD AND SYSTEM OF AUDITORY EVOKED HEART RATE VARIABILITY ANALYSIS

(75) Inventors: Guo-She Lee, Taipei (TW); Bo-Jau Kuo, Taipei (TW)

(73) Assignee: National Yang-Ming University, Taipei (TW)

( * ) Notice: Subject to any disclaimer, the term of this patent is extended or adjusted under 35 U.S.C. 154(b) by 411 days.

(21) Appl. No.: 12/503,513

(22) Filed: Jul. 15, 2009

(65) Prior Publication Data

US 2010/0268104 A1 Oct. 21, 2010

(30) Foreign Application Priority Data

Apr. 15, 2009 (TW) ................................ 098112525

(51) Int. Cl.
 *A61B 5/04* (2006.01)
(52) U.S. Cl.
 USPC .......................................... 600/509; 600/508
(58) Field of Classification Search
 USPC ........ 128/905; 600/508–509, 514; 607/55–57
 See application file for complete search history.

(56) References Cited

U.S. PATENT DOCUMENTS

| 5,291,400 | A | 3/1994 | Gilham |
| 6,512,945 | B1 * | 1/2003 | Hoium et al. ................. 600/515 |
| 6,811,536 | B2 | 11/2004 | Sun et al. |
| 7,277,746 | B2 * | 10/2007 | Kuo et al. .................... 600/509 |
| 2007/0167694 | A1 * | 7/2007 | Causevic et al. ............. 600/301 |

FOREIGN PATENT DOCUMENTS

| TW | 363404 | 7/1999 |
| TW | 225394 | 12/2004 |

* cited by examiner

*Primary Examiner* — Niketa Patel
*Assistant Examiner* — Mallika D Fairchild
(74) *Attorney, Agent, or Firm* — Muncy, Geissler, Olds & Lowe, PLLC (57) ABSTRACT

The present invention provides a method and system of auditory evoked heart rate variability analysis having advantage of simply analytical process and portability. The disclosed method mainly includes the following steps of: stimulating the auditory system of a person by a sound through a sound transmission device, capturing an electrocardiogram signal of the person, performing analog-to-digital conversion of the electrocardiogram signal, selecting the peaks of the electrocardiogram signal and transforming the qualified peaks to a consecutive peak signal, and performing spectrum analysis to the peak signal in frequency domain, and obtaining the difference of the spectral parameters before and after the evoked sounds. Moreover, the sound further is selected from the group consisting of noise, short tone burst, click, and any other sound with the intensity of 30 dB to 100 dB. By comparing the heart rate variability analysis before or after sound stimulation in order to get the differences, the disclosed method and system of auditory evoked heart rate variability analysis can evaluate a changing index of stimulated autonomic functions.

15 Claims, 6 Drawing Sheets

METHOD AND SYSTEM OF AUDITORY EVOKED HEART RATE VARIABILITY ANALYSIS

BACKGROUND OF THE INVENTION

1. Field of the Invention

The present invention generally relates to a method and system of heart rate variability analysis, and more particularly to a method and system of auditory evoked heart rate variability analysis for evaluating the reaction of human autonomic nervous system to sound stimulation and the function of autonomic nervous system.

2. Description of the Related Art

Human autonomic nervous system controls the physiological function relevant to life maintenance through the whole body, which comprises blood pressure, heart rate, tracheal resistance, perspiration, body temperature, and metabolism. These nerve operations can process automatically. Autonomic nervous system mainly includes sympathetic nerves and parasympathetic nerves. Generally speaking, the former is related to resist the environment, whereas the latter is related to propagation. For example, when a person is excited, the former will increase the blood pressure and dilate the pupils while the latter will cause gastrointestinal secretion and genital erection. In general, sympathetic functions and parasympathetic functions are active in young persons, but rather inactive in old persons; in males, sympathetic functions prevail but parasympathetic functions yield; conversely, parasympathetic functions excel sympathetic functions in females. So we can know that sympathetic nerves and parasympathetic nerves are closely related to the daily operation of a human body. Autonomic imbalance may induce various acute and chronic diseases, for example, heart disease, hypertension, etc., and may even lead to a sudden death, if serious. Hence, the protection for autonomic nervous system is not only an important issue in medicine but also a personal concern to an individual everyday. If we can control the function of autonomic nervous system efficiently, such as changing daily schedule, regulating respiratory frequency, and even processing the movement, relaxation, and reducing movement of the eyes, the diseases can be prevented or improved. Therefore, it will be an important regimen. The strong and weak of the sympathetic function are not only related to diseases, but also related to the variation of sleep, and alertness and concentration while awake. Detecting sympathetic function efficiently is helpful to improve the alertness and concentration while awake, or to decrease the alertness and concentration before sleep in order to promote falling asleep. In addition, controlling sympathetic function is also a common used method in psychology.

In recent years, plenty of new technologies to evaluate the autonomic functions were successfully developed. Given the sophisticated computer hardware and software know-how available, today it is possible to detect and perform quantitative analysis of a person autonomic cardiac activity in light of the minute fluctuations of hear rate, known as heart rate variability (HRV), taken while the person is at rest. In other words, the new technologies allow a user to analyze or evaluate a normal person's autonomic functions without interfering with the person's daily life. Researchers discovered that the minute fluctuations of heart rate variability, which can be represented by total power (TP), can be divided into two groups by frequency, that is, high-frequency (HF) component and low frequency (LF) component. The HF component is according to the rhythm of breath, so it is also known as breathing component. The source of the LF component is relevant to vascular motion or baroreflex.

Many physiologists and cardiologists believe that the HF component or total power reflects parasympathetic functions, whereas the ratio of LF component to HF component (LF/HF) reflects sympathetic activity. For instance, patients diagnosed with intracranial hypertension usually have relatively low heart rate variability. The public health investigation of American Framingham found that the death rate of an elder whose LF component of heart rate variability decreases by a standard deviation is 1.7 times that of normal person. Nowadays, a series of software and hardware, which can process spectrum analysis directed against various physiological signals on-line, have been developed. If the LF components of heart rate and blood pressure are the index of depth of anesthesia, for example, it can be found in the intensive care unit that the survival rates of patients decrease while heart rate variability decreases and the LF component of heart rate variability vanishes in a brain-dead person. Furthermore, there are changes in heart rate variability in a patient who exhibits rejection reactions after heart transplantation. However, the autonomic functions differ from person to person. The individual variation affects a lot. Sex, age, the variation of day and night, and etc. can result in the change of the autonomic functions. Moreover, the sounds also result in changes of autonomic nervous function, such that a great sound of more than 100 dB results in a startle reflex, and the long-term exposure to noise also increases the blood pressure. In addition, there are some clinical diseases, such as melancholia, migraine, tinnitus, and vertigo sensitive to sounds, which only can be estimated by the subjective feeling of patients or questionnaires instead of objective methods up to present.

According to the above problems, there is needed to provide an easy operating and sensitive method and system of auditory evoked heart rate variability analysis, which stimulate the auditory system by a sound and then measure the differences of heart rate variability before and after stimulation. The heart rate variability evoked by sounds, which individual variation is less and more sensitive, can predict or evaluate some specific diseases, especially some diseases which are sensitive to sounds. It can also estimate healthiness of autonomic nervous system.

BRIEF SUMMARY OF THE INVENTION

The primary objective of the present invention is to provide a method of auditory evoked heart rate variability analysis, with a view to evaluate the reaction of human autonomic nervous system to a sound stimulation. Furthermore, the present invention involves filtering out noise by means of statistical method, in order to enhance the precision of the analysis of heart rate variability.

The another objective of the present invention is to provide a system of auditory evoked heart rate variability analysis, by which the analytical process can be simplified, to be a sympathetic function examining technology of autonomic nervous system.

To achieve the first objective, the present invention provides a method of auditory evoked heart rate variability analysis which mainly comprises the following steps of: In a peaceful environment which noise is less than 50 dBA, a subject is requested to sit for 5 minutes and record the electrocardiogram for 5 minutes. Following, perform analog-to-digital conversion of the electrocardiogram signal and then measure the interval of the peaks of the electrocardiogram signal by digital signal processing, which the cycle of the heartbeat can be obtained. A smooth and continuous heartbeat cycle curve will be obtained by interpolation, eliminating outliers, and sampling. Finally, the heartbeat cycle curve performs a spectrum analysis to obtain the parameters of heart rate variability in time domain, which are benchmarks without external sound stimulation. After that, stimulate the auditory system of a person by a sound stimulation through a sound transmission device which can be speakers, earphones, or bone conduction earphones. The sound stimulation time is also 5 minutes. Capture the electrocardiogram signal of the object while stimulation and proceed heart rate variability analysis by analog-to-digital conversion. Following, the difference of autonomic nervous function with sound stimulation can be obtained by comparing the parameters of heart rate variability before and after stimulation, which will vary with the different types of the sound stimulation and the different diseases. In this mode, it can detect various diseases and estimate the results of curing disease.

According to one aspect of the present invention of a method of auditory evoked heart rate variability analysis, the sound is selected from the group consisting of noise, short tone burst, click, and other types of sound.

To achieve the second objective, the present invention provides a system of auditory evoked heart rate variability analysis which mainly comprises a sound source, an electrocardiogram signal converter, a micro-controller unit, a feature extraction unit, and a display unit. The sound source provides a sound through a sound transmission device to stimulate the auditory system of a person. The electrocardiogram signal converter is used for capturing an electrocardiogram signal of the person to proceed with heart rate variability. The micro-controller unit is used for processing the heart rate variability of the electrocardiogram signals. The feature extraction unit is used for capturing a feature of the heart rate variability from the micro-controller unit and sending it back to the micro-controller unit. The display unit is used for displaying the deciding result of the micro-controller unit.

According to one aspect of the present invention of a system of auditory evoked heart rate variability analysis, the feature extraction unit comprises of a time domain analysis of the heart rate variability and a frequency domain analysis of the heart rate variability.

The invention itself, though conceptually explained in above, can be best understood by referencing to the following description, taken in conjunction with the accompanying drawings.

BRIEF DESCRIPTION OF THE DRAWINGS

All the objects, advantages, and novel features of the invention will become more apparent from the following detailed descriptions when taken in conjunction with the accompanying drawings.

DETAILED DESCRIPTION OF THE INVENTION

Although the invention has been explained in relation to several preferred embodiments, the accompanying drawings and the following detailed descriptions are the preferred embodiment of the present invention. It is to be understood that the following disclosed descriptions will be examples of present invention, and will not limit the present invention into the drawings and the special embodiment.

Figure 1:
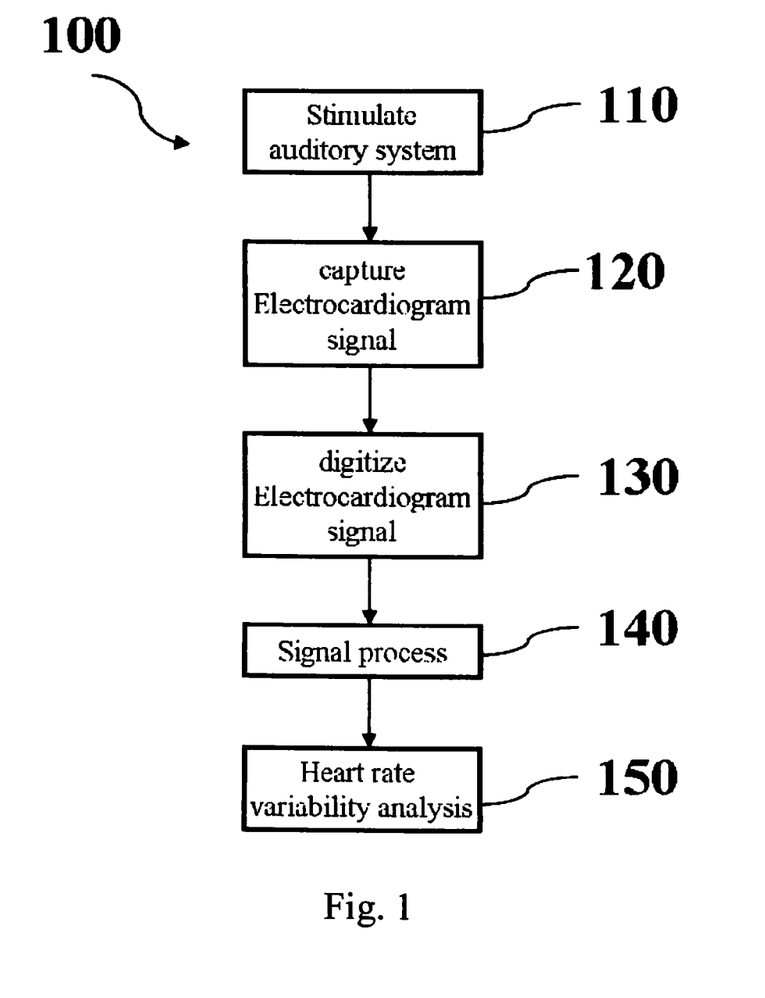
FIG. 1 shows a process flow chart of the method of auditory evoked heart rate variability analysis according to the present invention.

Referring to FIG. 1, it shows a process flow chart of the method of auditory evoked heart rate variability analysis 100 according to the present invention. The method of auditory evoked heart rate variability analysis 100 mainly comprises the following steps of: (1) stimulating the auditory system of a person 209 by a sound through a sound transmission device 208; (2) capturing an electrocardiogram signal 120 of the person 209; (3) performing analog-to-digital conversion 130 of the electrocardiogram signal; (4) proceeding signal processing 140, which measure the interval of the peaks of the electrocardiogram signal by digital signal processing, which the cycle of the heartbeat can be obtained. A smooth and continuous heartbeat cycle curve will be obtained by interpolation, eliminating outliers, and sampling. And then (5) performing a spectrum analysis. Moreover, the sound is selected from the group consisting of noise, short tone burst, click, and other sounds with the intensity of 30 dB to 100 dB. Additionally, the spectrum analysis, which the heartbeat cycle curve performs, comprises of a time domain analysis of the heart rate variability and a frequency domain analysis of the heart rate variability. Wherein, the sound transmission device 208 is selected from the group consisting of an earphone, horn, a megaphone, bone conduction earphones, and any device which can transmit the sound. Therefore, the difference of the spectral parameters before and after the evoked sounds can be obtained.

Figure 2:
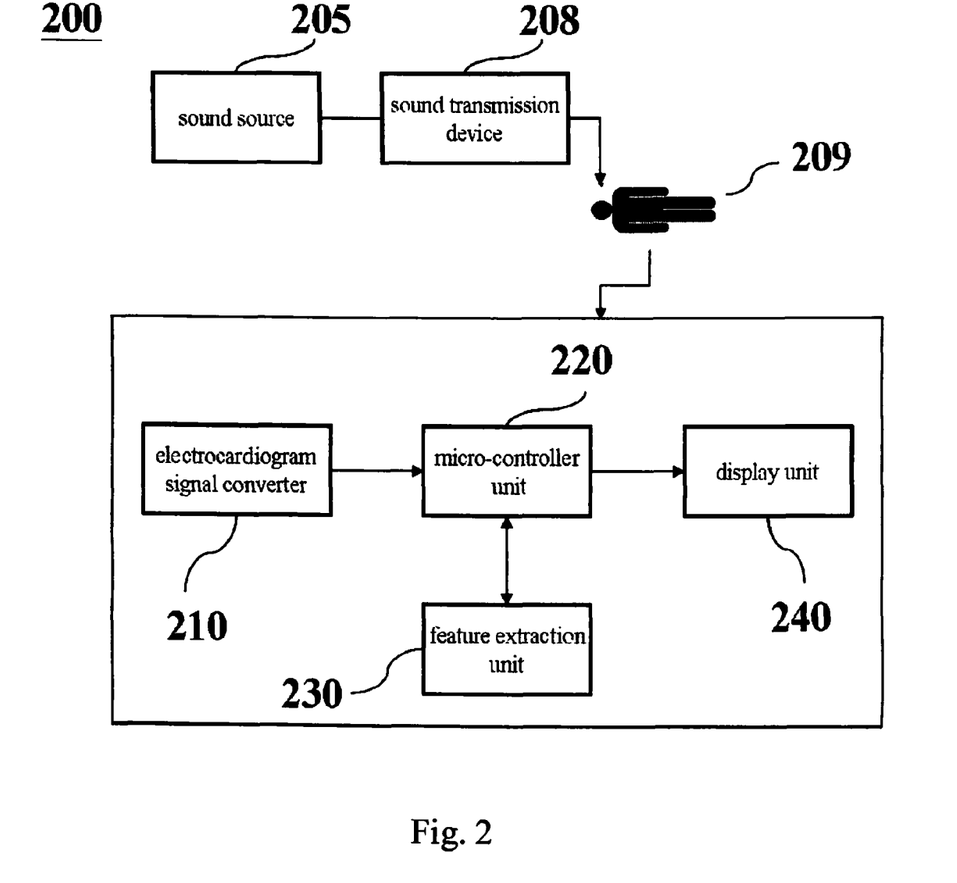
FIG. 2 shows a process flow chart of the system of auditory evoked heart rate variability analysis according to the present invention.

Referring to FIG. 2, it shows a process flow chart of the system of auditory evoked heart rate variability analysis 200 according to the present invention. The system 200 mainly comprises a sound source 205, an electrocardiogram signal converter 210, a micro-controller unit 220, a feature extraction unit 230, and a display unit 240. The display result of display unit 240 is selected from the group consisting of time, frequency domain analysis, and time domain analysis, and the display unit 240 is selected from the group consisting of the liquid crystal display and light emitting diode. It has to be noticed that the electrocardiogram signal converter 210, the micro-controller unit 220, the feature extraction unit 230, and the display unit 240 can be a combinative apparatus, while the sound source 205 is disposed outside the combinative apparatus separately. The sound source 205 provides a sound through a sound transmission device 208 to stimulate the auditory system of a person. The electrocardiogram signal converter 210 is used for capturing an electrocardiogram signal of the person 209 to proceed with heart rate variability. The micro-controller unit 220 is used for processing the heart rate variability of the electrocardiogram signal converter 210. The feature extraction unit 230 is used for capturing a feature of the heart rate variability from the micro-controller unit 220 and sending it back to the micro-controller unit 220. The display unit 240 is used for displaying the deciding result of the micro-controller unit 220. Furthermore, the micro-controller unit 220 reads automatically the electrooculography which will be calculated to obtain the autonomic nervous function, such as sympathetic nerves and parasympathetic nerves by various operating formula. Wherein, the sound transmission device 208 is selected from the group consisting of an earphone, a megaphone, and any device which can transmit the sound.

The feature extraction unit 230 is comprised of a time domain analysis of the heart rate variability and a frequency domain analysis of the heart rate variability. The time domain analysis of the heart rate variability can obtain heart rate and standard deviation of heart rate variability. Additionally, the frequency domain analysis of the heart rate variability can obtain the low frequency power, the high frequency power, and the ratio of the low frequency power divided by the high frequency power. Fourier transform is adopted in the frequency domain analysis. In the first place, any linear drift of signal is eliminated to evade the interference from low-frequency band, and the Hamming computation is employed to prevent the mutual leakage between individual frequency components of the spectrum. After that, fast Fourier transform is conducted so as to acquire heart rate power spectral density (HPSD), and the compensation with regard to any effects of sampling and Hamming computation is performed. The low frequency power (0.04-0.15 Hz) and the high frequency power (0.15-0.4 Hz) bands of the heart rate power spectral density are quantified by integral, and the quantitative parameters like the ratio of the low frequency power divided by the high frequency power are captured.

Figure 3:
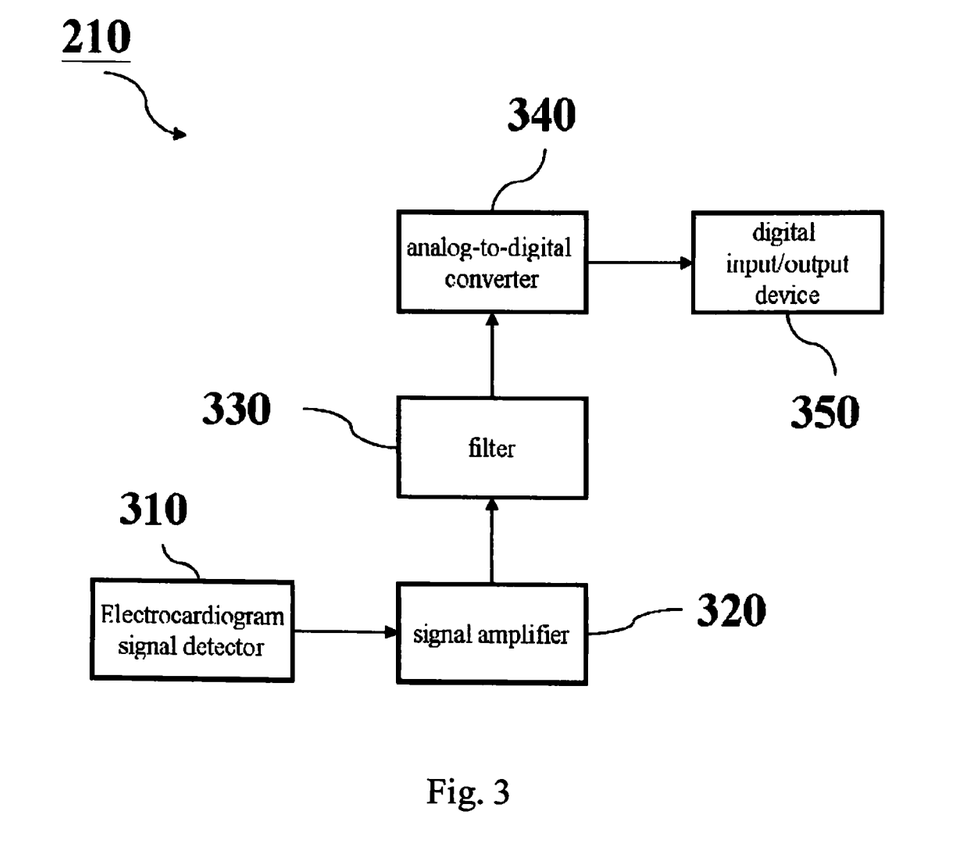
FIG. 3 shows a process flow chart of the electrocardiogram signal converter according to the present invention.

Referring to FIG. 3, it shows a process flow chart of the electrocardiogram signal converter 210 according to the present invention. U.S. Pat. No. 7,277,746 "Methods and Apparatus for Analyzing Heart Rate Variability", TW 363404 "electrocardiogram signal converter for Analyzing Heart Rate Variability", and TW 225394 "Methods and Apparatus for Analyzing Heart Rate Variability" issued to "Kuo, Terry B. J.", etc. are all cited as the reference in this invention. The electrocardiogram signal converter 210 comprises: an electrocardiogram signal detector 310; a signal amplifier 320; a filter 330; an analog-to-digital converter 340 and a digital input/output device 350. The electrocardiogram signal detector 310 is used for capturing the electrocardiogram signal, which is capturing the electrocardiogram signal of a person 209. The signal amplifier 320 is used for amplifying the electrocardiogram signal. The filter 330 is used for filtering the electrocardiogram signal. The analog-to-digital converter 340 is connected to the signal amplifier 320 for digitizing the electrocardiogram signal. The digital input/output device 350 is connected to the analog-to-digital converter 340 as a communication interface of the electrocardiogram signal. One end of each detection electrode is connected to the person 209, and the other end passes through the case to be connected to the signal amplifier 320 so as to capture a person 209 electrocardiogram signals and transmit them to the signal amplifier 320, which is used to proceed signal processing 140. After being amplified by the signal amplifier 320, the electrocardiogram signals are converted into heartbeat cycle curve of digital signals by means of the analog-to-digital converter 340, and then are entered into the micro-controller unit 220.

The micro-controller unit 220 executes a program to carry out a series of analyses and control-related tasks. The digital input/output device 350 functions as the transmission interface between the micro-controller unit 220 and the person 209. In practice, the digital input/output device 350 may be additionally connected to an indicator to be a user-machine interface intended for external communication. Transmission lines connect the signal amplifier 320 and the analog-to-digital converter 340, the analog-to-digital converter 340 and the micro-controller unit 220, and the micro-controller unit 220 and the digital input/output device 350 to transmit signals. It is deserved to be mentioned that the signal amplifier 320 and the filter 330 are one of differential amplifier and single-ended digital amplifier.

The types of the electronic components of the system of auditory evoked heart rate variability analysis 200 which can be implemented include: Bipolar Junction Transistor (BJT), Heterojunction Bipolar Transistor (HBT), High Electronic Mobility Transistor (HEMT), Pseudomorphic HEMT (PHEMT), Complementary Metal Oxide Semiconductor Filed Effect Transistor (CMOS) and Laterally Diffused Metal Oxide Semiconductor Filed Effect Transistor (LDMOS). Semiconductor materials broadly applicable to the electronic components of the analytical apparatus of heart rate variability include: silicon, silicon-on-insulator (SOI), silicon-germanium (SiGe), gallium arsenide (GaAs), indium phosphide (InP) and silicon-germanium-carbon (SiGe—C). Preferably, the electrocardiogram signal converter 210 is designed with resistive shunt-feedback PHEMT transistors on semiconductor substrate of Al—In—GaAs compound.

Figure 4:
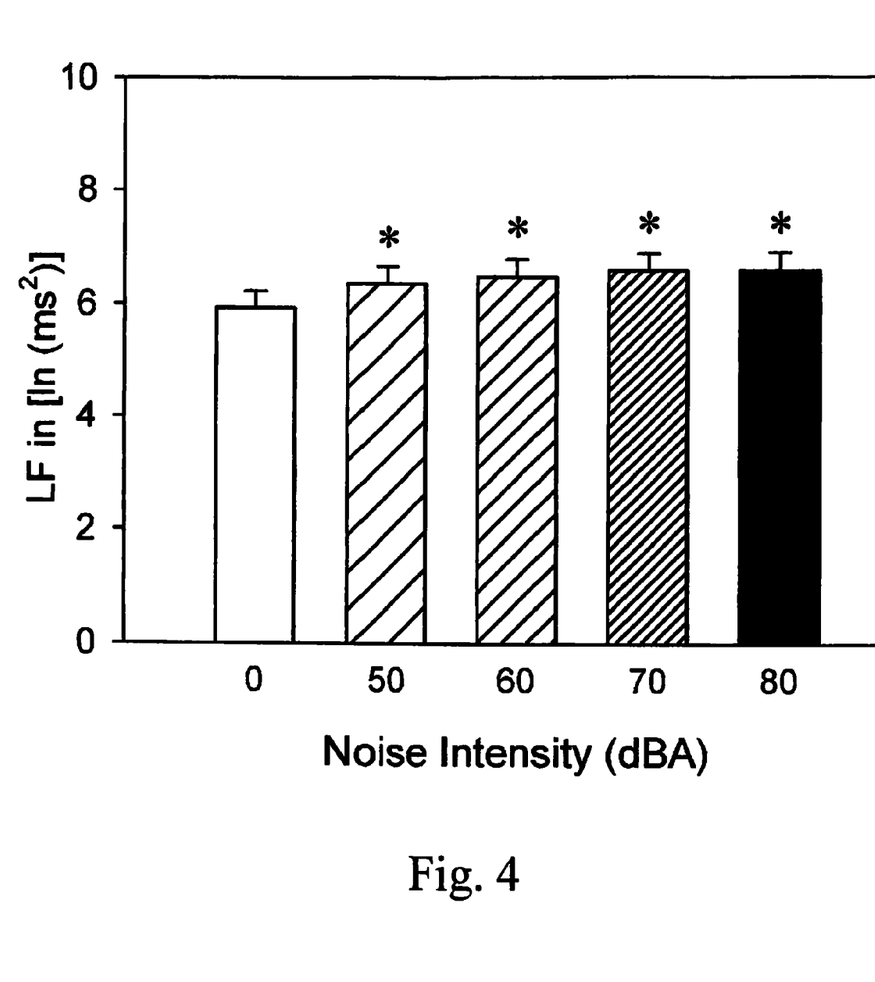
FIG. 4 shows changes of low frequency power (LF) of twelve healths whose auditory systems are under the stimulation of white noises with various intensities of 50 dB, 60 dB, 70 dB, and 80 dB.

In a practice, a person 209 is requested to sit for 5 minutes to adapt the surrounding, and then measure the electrocardiogram of the person 209 as a background. First, the person 209 is requested to wear an earphone without any sound, which the electrocardiogram of five minutes is collected to proceed with heart rate variability analysis. After that, the sounds, such as noises, short tone burst, and click, with a specific volume, such as 70 dB or more, are outputted through the earphone to stimulate the auditory system of the person 209. At the same time, the electrocardiogram of the person 209 is collected to proceed with heart rate variability analysis. Comparing the heart rate variability analysis between before or after sound stimulation, the difference can be obtained to do the correction with the intensity of sound stimulation. Or designate the difference obtained from the fixed stimulation volume as a change index of stimulated autonomic nervous system. The reaction parameters to sound stimulation includes low frequency power (LF) which reflects autonomic function and low high ratio (LHR) or low frequency percentage (LF %) which reflects sympathetic function. Referring to FIG. 4, it shows changes of low frequency power (LF) of twelve healths whose auditory systems 110 are under the stimulation of white noises with various intensities of 50 dB, 60 dB, 70 dB, and 80 dB. From the diagram, the LF, which increases as stimulation volume increasing, is related to the white noises with intensities of 50 dB, 60 dB, 70 dB, and 80 dB statistically.

Figure 5:
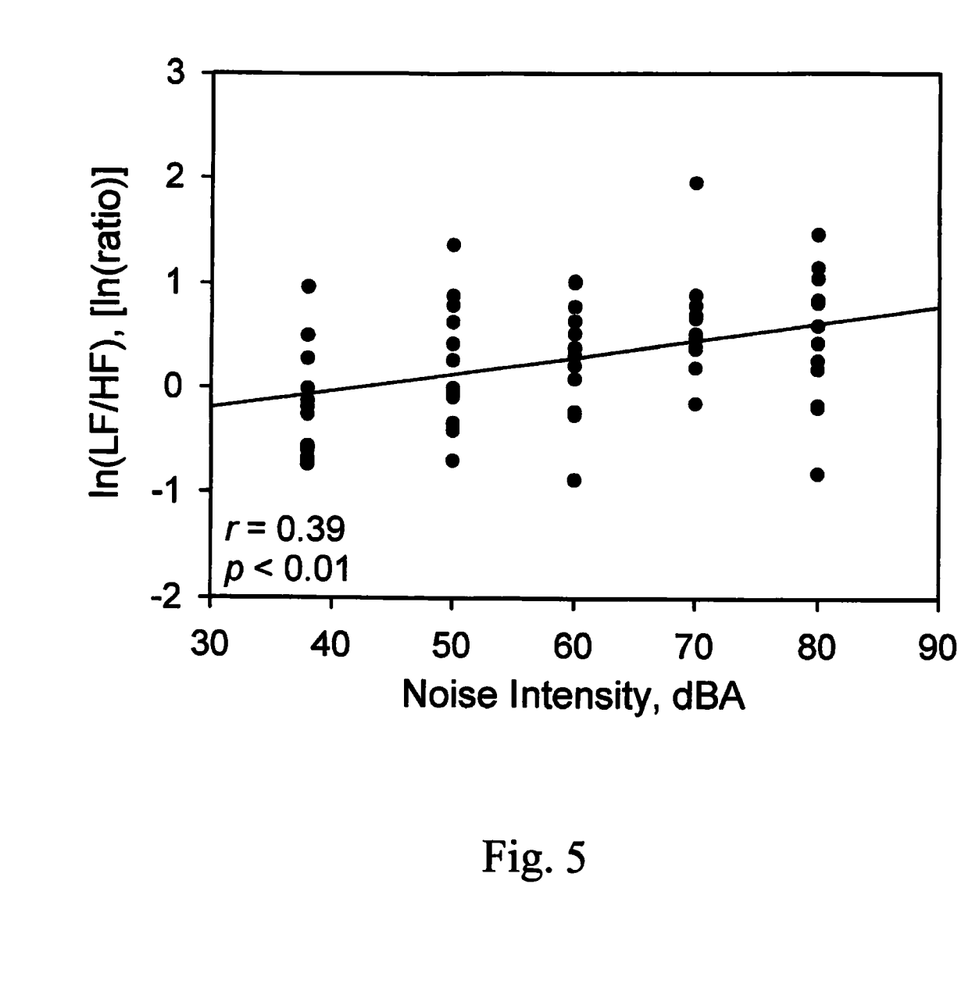
FIG. 5 shows an statistically related diagram between the low high ratio (LHR) of twelve healths, whose auditory systems are under the stimulation of white noises with various intensities, and the intensities of the noises.

Referring to FIG. 5, it shows a statistically related diagram between the low high ratio (LHR) of twelve healths, whose auditory systems 110 are under the stimulation of white noises with various intensities, and the intensities of the noises. From the diagram, the LHR, which increases as stimulation volume increasing, is related to the intensity of the noise statistically, which means the LHR reflected sympathetic function is linear to the intensity of the noise.

Figure 6:
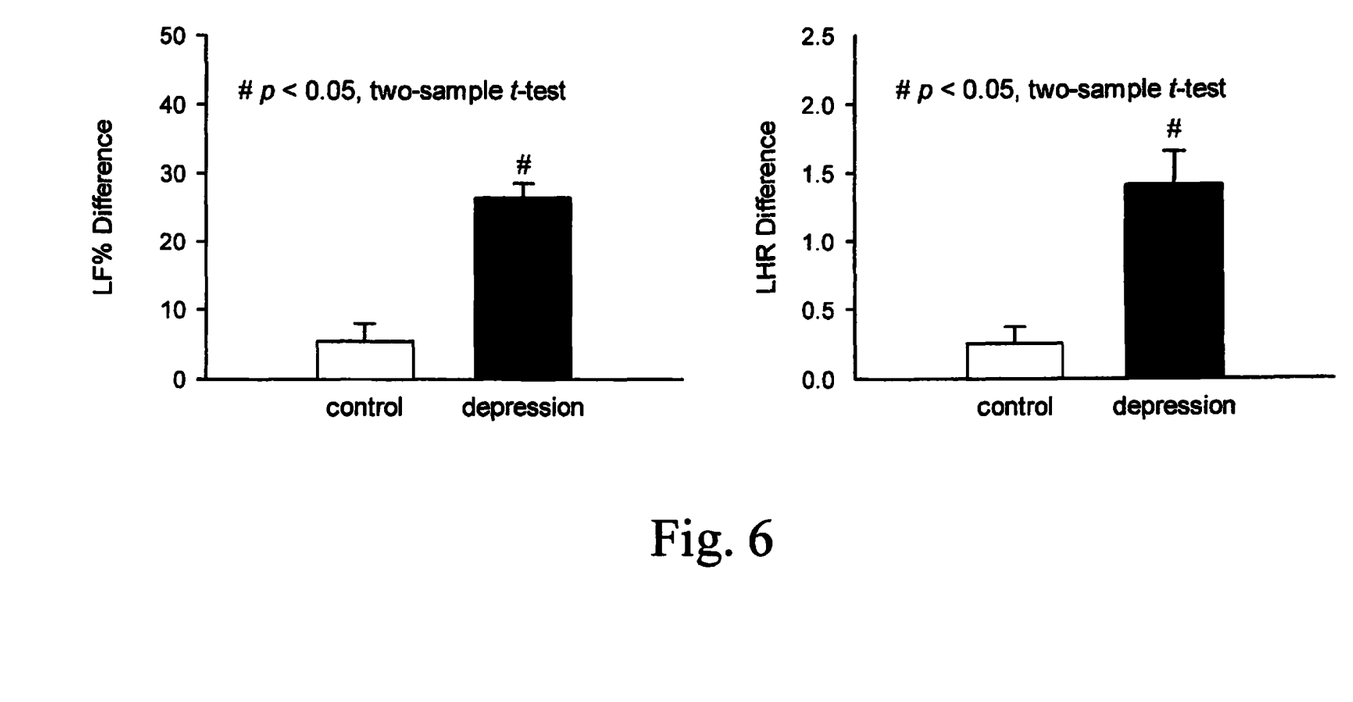
FIG. 6 shows analytical results of low frequency power (LF), low high ratio (LHR), and low frequency percentage (LF %) of some patients with migraine and melancholia comparing to healths, whose auditory systems are under the stimulation of white noises with various intensities.

Referring to FIG. 6, it shows analytical results of low frequency power (LF), low high ratio (LHR), and low frequency percentage (LF %) of some patients with migraine and melancholia (experimental group) comparing to healths (control group), whose auditory systems 110 are under the stimulation of white noises with various intensities. From the diagram, the raising amount of LF, LHR, and LF % of the patients with migraine and melancholia is larger than that of the healths after stimulation. Therefore, the method of auditory evoked heart rate variability analysis can be applied to basic or clinical medicine.

Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. A method of auditory evoked heart rate variability analysis for evaluating function of autonomic nervous system, comprising the following steps of:
    capturing a first electrocardiogram signal of a person with a first time period without any sound;
    stimulating the auditory system of the person by a sound with the intensity of the sound within 30 dB to 100 dB with a second time period through a sound transmission device;
    capturing a second electrocardiogram signal of the person under the sound;
    performing an analog-to-digital conversion of the first and the second electrocardiogram signals;
    selecting the peaks of the first and the second electrocardiogram signals after the analog-to-digital conversion and transforming peaks of the electrocardiogram signal to a first heartbeat cycle and a second heartbeat cycle curve, respectively;
    performing a spectrum analysis of the first heartbeat cycle and the second heartbeat cycle curve to obtain a first spectral parameter and a second spectral parameter; and
    obtaining a difference between the first spectral parameter and the second spectral parameter to obtain a change index of function of autonomic nervous system.

2. The method of auditory evoked heart rate variability analysis as claimed in claim 1, wherein the sound is selected from the group consisting of short tone burst, click and other noises, and the first time period and the second time period are around five minutes.

3. The method of auditory evoked heart rate variability analysis as claimed in claim 1, wherein the step of stimulating the auditory system of the person limits the sound intensity of the sound within 40 dB to 80 dB.

4. A method of auditory evoked heart rate variability analysis for evaluating function of autonomic nervous system, comprising the following steps of:
    capturing a first electrocardiogram signal of a person with a first time period without any sound;
    performing an analog-to-digital conversion of the first electrocardiogram signal;
    selecting the peaks of the first electrocardiogram signals after the analog-to-digital conversion and transforming the peaks of the electrocardiogram signal to a first heartbeat cycle;
    performing a spectrum analysis to the first heartbeat cycle to obtain a first spectral parameter;
    stimulating the auditory system of the person by a sound with the intensity of the sound within 30 dB to 100 dB with a second time period through a sound transmission device;
    capturing a second electrocardiogram signal of the person under the sound;
    performing the analog-to-digital conversion of the second electrocardiogram signal;
    selecting the peaks of the second electrocardiogram signal after the analog-to-digital conversion and transforming the peaks of the electrocardiogram signal to a second heartbeat cycle curve;
    performing a spectrum analysis to the second heartbeat cycle curve to obtain a second spectral parameter; and
    obtaining a difference between of the first spectral parameter and the second spectral parameter to obtain a change index of function of autonomic nervous system.

5. The method of auditory evoked heart rate variability analysis as claimed in claim 4, wherein the change index of function of autonomic nervous system for a patient with unsatisfied function of autonomic nervous system is N times compared to the change index of function of autonomic nervous system for a healthy person, and N is between 2 to 5.

6. A system of auditory evoked heart rate variability analysis for evaluating function of autonomic nervous system, comprising:
    a sound source;
    a sound transmission device, configured to provide a first sound to a person from the sound source with the intensity of the sound equal to 0 dB and effectively isolating a noise around the person in the background noises of intensity less than 50 dBA with a first time period, and a second sound to the person from the sound source with the intensity of the sound within 30 dB to 100 dB with a second time period to stimulate the auditory system of the person;
    an electrocardiogram signal converter, configured to capture a first electrocardiogram signal of the person under the first sound and a second electrocardiogram signal of the person under the second sound;
    a micro-controller unit, configured to process a first heart rate variability analysis from the first electrocardiogram signal, as a baseline hear rate variability analysis, and a second heart rate variability analysis of the electrocardiogram signal converter from the second electrocardiogram signal;
    a feature extraction unit, configured to capture a first feature of the first heart rate variability analysis and a second feature of the second heart rate variability analysis from the micro-controller unit and sending the first feature and the second feature back to the micro-controller unit and wherein the microcontroller unit is configured to obtain a difference between of the first feature and the second feature before and after the evoked sounds to obtain a change index of function of autonomic nervous system; and
    a display unit, configured to display the change index of function of autonomic nervous system of the micro-controller unit.

7. The system of auditory evoked heart rate variability analysis as claimed in claim 6, wherein the electrocardiogram signal converter comprises:
    an electrocardiogram signal detector, configured to capture the electrocardiogram signal of the person;
    a signal amplifier, electrically connected to the electrocardiogram signal detector, configured to amplify the first and the second electrocardiogram signals;
    a filter, electrically connected to the signal amplifier, configured to filter the first and the second electrocardiogram signals;
    an analog-to-digital converter, electrically connected to the filter, configured to digitize the first and the second electrocardiogram signals; and a digital input/output device, electrically connected to the analog-to-digital converter, configured as a communication interface of the electrocardiogram signal.

8. The system of auditory evoked heart rate variability analysis as claimed in claim 6, wherein the feature extraction unit comprises of a time domain analysis of the heart rate variability and a frequency domain analysis of the heart rate variability.

9. The system of auditory evoked heart rate variability analysis as claimed in claim 8, wherein the time domain analysis of the heart rate variability can obtain heart rate and standard deviation of heart rate variability.

10. The system of auditory evoked heart rate variability analysis as claimed in claim 8, wherein the frequency domain analysis of the heart rate variability using a fast Fourier transform and a Hamming computation can obtain a heart rate power spectral density (HPSD), having a plurality of spectral parameters, comprising a low frequency power of the heart rate power spectral density, a high frequency power of heart rate power spectral density, a percentage of low frequency power of the heart rate power spectral density, and a low high ratio (LHR) for the low frequency power divided by the high frequency power.

11. The system of auditory evoked heart rate variability analysis as claimed in claim 6, wherein the first time period and the second time period are around five minutes.

12. The system of auditory evoked heart rate variability analysis as claimed in claim 6, wherein the display unit is selected from the group consisting of the liquid crystal display and light emitting diode.

13. The system of auditory evoked heart rate variability analysis as claimed in claim 7, wherein the signal amplifier and the filter are selected from the group consisting of differential amplifier and single-ended digital amplifier.

14. The system of auditory evoked heart rate variability analysis as claimed in claim 10, wherein the change index of function of autonomic nervous system is related to the intensity of the noise statistically and linearly.

15. The system of auditory evoked heart rate variability analysis as claimed in claim 7, wherein the change index of function of autonomic nervous system for a patient with unsatisfied function of autonomic nervous system is N times compared to the change index of function of autonomic nervous system for a healthy person, and N is between 2 to 5.

* * * * *